United States Patent [19]

Knebel et al.

[11] Patent Number: 4,745,224

[45] Date of Patent: May 17, 1988

[54] METHODS FOR MAKING TERTIARY PHOSPHINE OXIDES

[75] Inventors: Joachim Knebel; Werner Ude, both of Darmstadt, Fed. Rep. of Germany

[73] Assignee: Röhm GmbH, Darmstadt, Fed. Rep. of Germany

[21] Appl. No.: 937,200

[22] Filed: Dec. 2, 1986

[30] Foreign Application Priority Data

Dec. 13, 1985 [DE] Fed. Rep. of Germany ....... 3544065

[51] Int. Cl.$^4$ .............................................. C07F 9/02
[52] U.S. Cl. ..................................................... 568/14
[58] Field of Search ......................................... 568/14

[56] References Cited

U.S. PATENT DOCUMENTS

| | | | |
|---|---|---|---|
| 3,082,256 | 3/1965 | Harwood et al. | 260/606.5 |
| 4,101,655 | 7/1978 | Sukman | 424/204 |
| 4,371,509 | 2/1983 | Grosse | 423/300 |
| 4,492,805 | 1/1985 | Bescke et al. | 568/12 |
| 4,511,738 | 4/1985 | Tokuyama et al. | 568/14 |

FOREIGN PATENT DOCUMENTS 49342 4/1982 Fed. Rep. of Germany .
2113225 8/1983 United Kingdom .

OTHER PUBLICATIONS

Luckenbach et al., Chem. Ber. 108, 3533–3537 (1975).
Phosphorus 1974, 5(1), pp. 43–45.
Synthesis 1973, p. 307.
=Chem. Abstr. 79, 78888w (1973).
Helv. Chim. Acta. 47 (1964), 120–132.
Tetrahedron Letters, 21 (1980), 4421–4424.
Chem. Ind. [London], 1981 [10], 365–366.
J. Am. Chem. Soc. 74 (1921), 4526–4528.
Synthesis 1983, pp. 509–510.
J. Org. Chem. 38 (1973), 4071–4073.
Houben-Weyl, *Methoden der organischen Chemie*, 4th ed., vol. XII/1 (1963), pp. 135–141; op. cit.; vol. E2 (1982), pp. 41–50; op. cit., vol. E2 (1982), pp. 77–91.
Mem. Fac. Eng., Osaka City Univ. 4 (1962), 173–175.

*Primary Examiner*—Paul F. Shaver
*Attorney, Agent, or Firm*—Curtis, Morris & Safford

[57] ABSTRACT

Methods for making tertiary phosphine oxides from the corresponding tertiary phosphine sulfides by reacting the latter with sulfuric acid and/or organic sulfonic acids at temperatures from 70° C. to 200° C.

12 Claims, No Drawings

METHODS FOR MAKING TERTIARY PHOSPHINE OXIDES

The present invention relates to methods for making tertiary phosphine oxides.

Phosphine oxides are compounds of commercial interest which find use as complexing agents in homogeneous catalysis, for example, or as monomers for the production of difficulty combustible, highly heat resistant plastics, or in pesticides.

THE PRIOR ART

The known methods of preparing tertiary phosphine oxides are described in Houben-Weyl, "Methoden der organischen Chemie" (Georg Thieme Verlag), 4th ed., Vol. XII/1 (1963), pp. 135 et seq., and Vol. E 2 (1982), pp. 41 et seq. Important preparative methods are, on the one hand, those in which tertiary phosphines are used as starting materials and the phosphine oxide structure is formed directly by means of oxidizing agents or from tertiary phosphine dihalides as intermediate products, after hydrolysis with water or aqueous alkalis, and, on the other hand, methods starting out with tertiary phosphine sulfides and exchanging the sulfur for oxygen by means of oxidizing agents.

For preparing phosphorus-containing polyarylene ethers by polycondensation, as described in German patent No. 32 03 186 (U.S. Pat. No. 4,492,805) for example, functional tertiary phosphine oxides are used, and particularly haloarylphosphine oxides of the formula

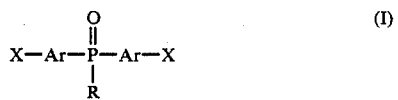

$$X-Ar-\overset{\overset{O}{\|}}{\underset{R}{P}}-Ar-X \qquad (I)$$

wherein Ar is, in particular, phenylene, X is halogen, and more particularly fluorine or chlorine, and R is alkyl, aryl or Ar—X.

Such compounds, or the corresponding phosphines as intermediates, can be prepared by means of the Grignard reaction, the Grignard reagents, such as 4-chlorophenylmagnesium bromide, being reacted with alkyldichlorophosphine oxides or aryldichlorophosphines oxides for example, or with alkyldichlorophosphines or aryldichlorophosphines. Reactions of this type are described in Mem. Fac. Eng., Osaka City Univ. 4 (1962) 173-175 (cf. Chem. Abstr. 59, 8782), in Phosphorus 1974, 5 (1), 43-45, and in U.S. Pat. No. 4,101,655.

However, the Grignard reaction is not suitable for the commercial production of haloarylphosphine oxides, or of the corresponding phosphines as intermediates, because the Grignard compounds employed are expensive and because the reaction is not easy to manage.

Another interesting route to the preparation of tertiary phosphine oxides, and particularly of those with functional groups, is by way of the tertiary phosphine sulfides. The latter can be readily prepared under Friedel-Crafts conditions according to Helv. Chim. Acta 47 (1964), 120-132. Numerous methods are known for preparing triorganylphosphine oxides from the corresponding sulfides. It is effected by reaction with thionyl chloride by way of chlorinated phosphorus intermediate stages (U.S. Pat. No. 3,082,256), or with alkali metal alcoholate-halogen or alkali metal-halogen compounds (British Patent No. 2,113,225), with dimethyl sulfoxide in an acidic solution (Synthesis 1973, 307), with polyphosphoric acid or a P$_2$O$_5$-methanesulfonic acid reagent (Tetrahedron Letters 1980, 21 (46), 4421-4424), photolytically in the presence of N-oxides (Chem. Ind. [London] 1981 [10], 365-366), and with strong oxidizing agents such as potassium permanganate or nitric acid (J. Am Chem Soc. 74, 4526 [1921]) or ozone (Synthesis 1983, [6], 509-510). However, the commercial practice of these processes is afflicted with serious drawbacks. For example, either toxic and/or costly reagents are used or by-products which are difficult to dispose of are obtained in the reactions.

THE OBJECTS AND FEATURES OF THE INVENTION

In the past, sulfur-oxygen exchange in tertiary phosphine sulfides has had preparative significance only in some cases since, as pointed out earlier, tertiary phosphines can often be converted to the corresponding phosphine oxides with oxygen alone. However, this advantageous method fails in the case of triarylphosphines such as tris(haloaryl)phosphines or bis(haloaryl)aryl- or bis(haloaryl)alkyl-phosphines, which find use in the production of difficulty combustible to noncombustible plastics resistant to high termperatures.

The object of the present invention is to produce phosphine oxides, as needed for the production of polymers containing phosphine oxide groups for example, from phosphine sulfides, and particularly from arylphosphine sulfides, by a simple process that can be carried out with low-cost reagents.

Surprisingly, it has been found that the reaction of tertiary phosphine sulfides generally with sulfuric acid or organosulfonic acids alone, with heating, will furnish the desired phosphine oxides in high yields. The reaction is very easy to manage. The phosphine sulfide is dissolved in the acid, optionally with heating, and the mixture is then heated until the phosphine sulfide has been completely converted. The conversion can be monitored analytically by thin layer chromatography, for example. The phosphine oxide is then isolated from the reaction mixture, for example by extracting with water.

With the method of the invention, the tertiary phosphine oxides are obtained even as crude products with purities of about 80 to 100 percent and in yields of about 80 to 100 percent of theory. The only by-products formed are elemental sulfur and sulfur dioxide, which are either filtered off or removed by absorption, for example in a sodium hydroxide solution.

ADVANTAGES OF THE INVENTION

The oxygenating desulfurization of tertiary phosphine sulfides solely by sulfuric acid or by sulfonic acids, the organic derivatives of sulfuric acid, is surprising since according to the prior art 50 percent aqueous sulfuric acid produces no sulfur-oxygen exchange in tertiary phosphines but is merely a proton donor for the exchange with the exchange reagent dimethyl sulfoxide (Synthesis 1973, 307). Similarly, according to J. Org. Chem. 38, 4071 (1973) and the applicants' own experiments, methanesulfonic acid under the conditions cited acts practically only as a solvent for phosphorus pentoxide, which acts like polyphosphoric acid, a known exchange reagent (Tetrahedron Letters 1980, 21 [46], 4421-4424).

The method of the invention makes it possible to produce phosphine oxides from phosphine sulfides without by-products—for example those formed by the oxidation of aliphatic groups—being obtained, as in the prior art processes employing strong oxidizing agents. Also, the yields and purities of the phosphine oxides are not significantly reduced by nitrated products, or by chlorophosphoranes as when thionyl chloride is used. Sulfuric acid as well as the organosulfonic acids, such as alkylsulfonic and arylsulfonic acids, and particularly methanesulfonic and toluenesulfonic acids, are reagents produced on a commercial scale that are relatively inexpensive, and this is true especially of sulfuric acid, which is one of the cheapest chemicals around.

The invention makes it possible to produce difunctional and trifunctional haloarylphosphine oxides, for example bis(chlorophenyl)methylphosphine oxide or tris(fluorophenyl)phosphine oxide, as needed for the preparation of polycondensation products, in high yields and at relatively low cost. Quite generally, however, the process of the invention permits tertiary phosphine sulfides (II) having aliphatic and/or aromatic groups which, moreover, may be substituted, to be converted to the corresponding tertiary phosphine oxides (III) in high yield and high purity in a sample manner in accordance with the following equation:

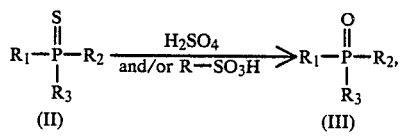

wherein
R is alkyl having from 1 to 6 carbon atoms or aryl, and in particular phenyl or tolyl, and
$R_1$, $R_2$ and $R_3$ are alkyl having from 1 to 10 carbon atoms, cycloalkyl having from 5 to 10 carbon atoms, aryl having from 6 to 10 carbon atoms, or aralkyl having from 7 to 10 carbon atoms.

These organo substituents may be the same or different and may have substituents thereon, for example halogen such as fluorine, chlorine, or bromine, or OR, wherein R has the meaning given above.

PRACTICE OF THE INVENTION

Tertiary phosphine sulfides for use as starting compounds for the practice of the process of the invention can be produced by known methods, as reviewed in Houben-Weyl, "Methoden der organischen Chemie" (Georg Thieme Verlag), 4th ed., Vol. E 2, pp. 77–91. Methods by which arylphosphine sulfides are advantageously obtained as intermediate products for the production of the corresponding phosphine oxides are of special importance. For example, phosphorus halosulfides such as dialkyl-, alkylaryl- and diaryl-thiophosphinic acid chlorides, alkyl- and aryl-thiophosphonic acid dichlorides, or thiophosphoric acid trichloride can be arylated under Friedel-Crafts conditions in the manner described in Helv. 47 (1964), 120–132. For arylation, benzene, toluene, fluorobenzene, chlorobenzene, bromobenzene, diphenyl ether, or phenylaryl ether may be used. $C_2H_5AlCl_2$ or $AlBr_3$ are suitable for use as Friedel-Crafts catalysts for carrying out the arylation for example, and particularly $AlCl_3$. Thus, haloarylphosphine sulfides which are intermediate products for the production of haloarylphosphine oxides having the structure (I) can also be produced. Arylphosphine sulfides of the formula (II), and in particular haloarylphosphine sulfides which carry cycloalkyl groups, and in particular cyclohexyl, or aryl groups, and particularly phenyl and toluene, are also obtainable in this manner as further substituents.

The tertiary thiophosphines to be converted in accordance with the invention may also be of a different origin. For example they may be formed in the reaction of phosphorus halosulfides with organometallic compounds when a low cost synthetic route will not yield the desired compound.

The sulfur-oxygen exchange reagents to be used in accordance with the invention are sulfuric acid and organic derivatives of sulfuric acid, the so called sulfonic acids. Sulfuric acid is used as 70 percent to 100 percent acid, advantageously as an 80 percent to 100 percent acid, and more particularly as commercial concentrated sulfuric acid with an acid content of about 96 percent, hereinafter "concentrated sulfuric acid".

Of the organic derivatives of sulfuric acid, both alkanesulfonic acids and aromatic sulfonic acids will produce the oxygenating desulfurization of tertiary phosphine sulfides. Usable alkanesulfonic acids are methanesulfonic acid as well as ethane-, propane-, butane-, pentane-, and/or hexane-sulfonic acid, i.e. suitably those having 1–6 carbon atoms. In compounds having three or more carbon atoms, the sulfonic acid groups may be located on different carbon atoms of the alkyl group. These compounds have melting points of not over 20° C. and can therefore be readily handled as reagents having the properties of a reaction medium.

Aromatic sulfonic acids suitable for use as sulfur-oxygen exchange reagents include, in addition to benzenesulfonic acid, toluenesulfonic acid (used primarily as a mixture of isomers), as well as xylenesulfonic acids or chlorobenzenesulfonic acids, for example 4-chlorobenzenesulfonic acid, as well as the corresponding aryldisulfonic acids. The organic sulfuric acid derivatives may also be used together with sulfuric acid as reagents. The molar ratio of thiophosphine to sulfuric acid or sulfuric acid compounds normally ranges from not less than 1:1 to 1:50, and advantageously from 1:2 to 1:30. The reaction may also be carried out in the presence of aprotic solvents such a methylene chloride or other fluorine- or chlorine-containing aliphatic or aromatic hydrocarbons, for example 1,2-dichlorotetrafluoroethane or chlorobenzene, cyclohexane, or methylcyclohexane. The reaction can be accelerated by heating the reaction mixtures to temperatures ranging from 70° C. to 250° C., and preferably from 110° C. to 200° C. The use of pressure normally is not necessary in carrying out the reaction. However, pressure may be build up in closed equipment as a function of temperature and of the then prevailing vapor pressures of the components present in the reaction. Isolation of the reaction products is effected by extraction of the reaction mixture, diluted with water, with an organic solvent such as methylene chloride, for example.

A better understanding of the invention and of its many advantages will be had by referring to the following Examples, given by way of illustration.

EXAMPLE 1

Preparation of 4,4'-difluorotriphenylphosphine oxide 5 g (15 mmols) 4,4'-difluorotriphenylphosphine sulfide are introduced into 3 ml of water and mixed with 28 ml of 96% $H_2SO_4$ (0.5 mol) with cooling. The batch is then heated for 4 hours at 140° C. to 150° C. After cooling to room temperature, the batch is mixed with 300 g of ice and extracted repeatedly with toluene. The toluene fractions are washed with Na₂CO₃ solution and, after drying over Na₂SO₄ and removal of the toluene in a vacuum, 4 g of a yellowish solid (85% of theory) are obtained which is identified by mass spectroscopy as 4,4′-difluorotriphenylphosphine oxide.

EXAMPLE 2

Preparation of bis(4-fluorophenyl)methylphoshine oxide 5 g (19 mmols) of bis(4-fluorophenyl)methylphosphine sulfide are mixed with 15 ml of 96% H₂SO₄ (0.27 mol). The mixture is heated for 2 hours at 140° C. to 150° C. After working up as in Example 1 (using dichloromethane as an extractant), 4.5 g (94% of theory) of bis(4-fluorophenyl)methylphosphine oxide, identified by mass spectroscopy, are obtained.

EXAMPLE 3

Preparation of 4,4′-dichlorotriphenylphosphine oxide 5 g (14 mmols) of 4,4′-dichlorotriphenylphosphine sulfide are mixed with 15 ml of 96% H₂SO₄ (0.27 mol). The mixture is heated for 4 hours at 140° C. to 150° C. After working up as in Example 1 (using dichloromethane as an extractant), 4.3 g (88% of theory) of 4,4′-dichlorotriphenylphosphine oxide, identified by mass spectroscopy, are obtained.

EXAMPLE 4

Preparation of triphenylphosphine oxide 5 g (17.5 mmols) of triphenylphosphine sulfide are mixed with 15 ml of 96% H₂SO₄ (0.27 mol). The mixture is heated for 9 hours at 140° C. to 150° C. After working up as in Example 2, 3.8 g are obtained of a product which, according to liquid-chromatographic analysis, is composed to the extent of 80% of triphenylphosphine oxide.

EXAMPLE 5

Preparation of tris(4-chlorophenyl)phosphine oxide 5 g (13 mmols) of tris(4-chlorophenyl)phosphine sulfide are mixed with 39.4 g of 85% H₂SO₄ (0.34 mol). The mixture is heated for 4 hours at 140° C. to 150° C. After working up as in Example 2, 4.5 g (90%) of tris(4-chlorophenyl)phosphine oxide are obtained. Identification is made by mass spectroscopy.

EXAMPLE 6

Preparation of 4,4′-difluorotriphenylphosphine oxide 5 g (15 mmols) of 4,4′-difluorotriphenylphosphine sulfide are mixed with 10 ml (0.15 mol) of methanesulfonic acid. The mixture is heated for 17 hours at 160° C. After working up as in Example 2, 4.6 g (98% of theory) of 4,4′-difluorotriphenylphosphine oxide of a purity of 96%, as determined by gas chromatography, are obtained.

EXAMPLE 7

Preparation of tri-n-butylphosphine oxide 5 g (21 mmols) of tri-n-butylphosphine sulfide are mixed with 30 ml of 96% H₂SO₄ (0.54 mol). The mixture is heated for 4 hours to 140° C. to 150° C. After working up as in Example 2, 4.3 g are obtained of a product which, according to gas-chromatographic analysis, contains 86% of tri-n-butylphosphine oxide and 14% of tri-n-butylphosphine sulfide.

EXAMPLE 8

Preparation of dicyclohexylmethylphosphine oxide 3.66 g (15 mmol) of dicyclohexylmethylphosphine sulfide in 60 ml of toluene (b.p. =110° C.) are heated for 6 hours under reflux with 34.4 g (0.2 mol) of p-toluenesulfonic acid. The product was then worked up as in Example 1. 3.0 g of solid are obtained which are identified by mass spectroscopy as dicyclohexylmethylphosphine oxide.

EXAMPLE 9

Preparation of triisoamylphosphine oxide 4.1 g (15 mmol) of triisoamylphosphine sulfide in 70 ml of chlorobenzene (b.p.=132° C.) are combined with 34.7 g (0.18 mol) of p-chlorobenzenesulfonic acid and then heated for 8 hours at reflux. After cooling to room temperature, the reaction mixture is extracted several times with 80 ml portions of ice water and then the chlorobenzene solution is washed with sodium bicarbonate solution. The solution is dried over sodium sulfate and the chlorobenzene is removed in vacuum. Yield: 3 g of solid identified by mass spectroscopy as triisoamylphosphine oxide.

EXAMPLE 10

Preparation tri-p-tolyphosphine oxide 6.7 g (20 mmol) of tri-p-tolyphosphine sulfide are combined with 66.5 g (0.40 mol) of n-hexylsulfonic acid in 100 ml of toluene (b.p.=110° C.). The mixture is heated for 8 hours at reflux temperature. After working up as in Example 9, 5 g of solid are obtained which are identified by mass spectroscopy as tri-p-tolyphosphine oxide.

EXAMPLE 11

Preparation of trimethylphosphine oxide 1.6 g (15 mmol) of trimethylphosphine sulfide in 50 ml of dichloromethane are combined with a mixture of 7.5 ml of sulfuric acid (96%) and 10 ml of methanesulfonic acid (0.15 mol). The mixture is heated for 10 hours in a closed vessel at 70° C. and is then worked up as in Example 9. 1 g of trimethylphosphine oxide, identified by mass spectroscopy, is obtained.

What is claimed is:

1. A method for making a tertiary phosphine oxide of the formula

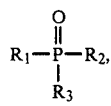

wherein R₁, R₂, and R₃ are alkyl having from 1 to 10 carbon atoms, cycloalkyl having from 5 to 10 carbon atoms, aryl having from 6 to 10 carbon atoms, or aralkyl having from 7 to 10 carbon atoms, which method comprises reacting the corresponding tertiary phosphine sulfide at a temperature from 70° C. to 250° C. with at least one sulfur-oxygen exchange reagent selected from the group consisting of sulfuric acid of at least 70 percent concentration and sulfonic acids of the formula R—SO$_3$H wherein R is alkyl having 1 to 6 carbon atoms or aryl.

2. A method as in claim 1 wherein said exchange reagent is sulfuric acid.

3. A method as in claim 1 wherein said exchange reagent is a sulfonic acid.

4. A method as in claim 1 wherein said exchange reagent is a mixture of sulfuric acid and sulfonic acid.

5. A method as in claim 1 wherein said sulfuric acid is 80% to 100% sulfuric acid.

6. A method as in claim 1 wherein said sulfuric acid is concentrated sulfuric acid.

7. A method as in claim 1 wherein said sulfonic acid is an aliphatic sulfonic acid having from 1 to 6 carbon atoms.

8. A method as in claim 1 wherein said sulfonic acid is an aromatic sulfonic acid.

9. A method as in claim 1 wherein from 1 to 50 mols of said exchange reagent of acid are used per mol of phosphine sulfide.

10. A method as in claim 1 wherein from 2 to 30 mols said exchange reagent are used per mol of phosphine sulfide.

11. A method as in claim 1 carried out at a temperature from 110° C. to 200° C.

12. A method as in claim 1 carried out in the presence of an inert aprotic solvent.

* * * * *